US012649902B2

(12) United States Patent
Wu Li et al.

(10) Patent No.: US 12,649,902 B2
(45) Date of Patent: Jun. 9, 2026

(54) HIGH-EXPRESSION TYPE MESENCHYMAL STEM CELLS, CULTURE METHOD AND USE THEREOF

(71) Applicant: Gwo Xi Stem Cell Applied Technology Co., Ltd., Zhubei (TW)

(72) Inventors: Wei Wu Li, Zhubei (TW); Tzyy-Wen Chiou, Zhubei (TW); Horng-Jyh Harn, Zhubei (TW); Shinn-Zong Lin, Zhubei (TW); Ming-Hsi Chuang, Zhubei (TW); Po-Cheng Lin, Zhubei (TW); Chia-Hsin Lee, Zhubei (TW); Mao-Hsuan Huang, Zhubei (TW)

(73) Assignee: Gwo Xi Stem Cell Applied Technology Co., Ltd., Zhubei (TW)

( * ) Notice: Subject to any disclaimer, the term of this patent is extended or adjusted under 35 U.S.C. 154(b) by 736 days.

(21) Appl. No.: 18/055,409

(22) Filed: Nov. 14, 2022

(65) Prior Publication Data

US 2023/0407262 A1 Dec. 21, 2023

(30) Foreign Application Priority Data

Jun. 21, 2022 (TW) ................................. 111122945

(51) Int. Cl.
| | |
|---|---|
| *C12N 5/0775* | (2010.01) |
| *A61K 38/17* | (2006.01) |
| *A61P 25/00* | (2006.01) |
| *C07K 14/435* | (2006.01) |
| *C12N 5/079* | (2010.01) |

(52) U.S. Cl.
CPC ............ *C12N 5/0663* (2013.01); *A61K 38/17* (2013.01); *A61P 25/00* (2018.01); *C07K 14/435* (2013.01); *C12N 5/0618* (2013.01)

(58) Field of Classification Search
None
See application file for complete search history.

(56) References Cited

PUBLICATIONS

Xu et al., Long non-coding Rna GAS5 controls human embryonic stem cell self-renewal by maintaining Nodal signalling, 2016, Nature communications, online publication, p. 1-18 (Year: 2016).*
Schier, Nodal Morphogens, 2009, Cold Spring Harbor Perspectives in Biology, online publication, p. 1-20 (Year: 2009).*
Belotti et al., Thrombospondin-1 promotes mesenchymal stromal cell functions via TGFb and in cooperation with PDGF, 2016, Matrix Biology, vol. 55, p. 106-116 (Year: 2016).*
Pagani et al., Heparin protects human neural progenitor cells from Zika Virus-induced cell death and preserves their differentiation into mature neural-glia cells, 2021, Online publication (bioRxiv), p. 1-50 (Year: 2021).*

* cited by examiner

*Primary Examiner* — Tracy Vivlemore
*Assistant Examiner* — Hanna Marie Thueson

(57) ABSTRACT

The present invention provides a medicine for treating a neurodegenerative disease, which employs LEFTY2 (Left-Right Determination Factor 2) generated by co-culturing mesenchymal stem cells of mammals with nerve cells having mutations in the APP (Amyloid precursor protein) gene, or a specific protein. The LEFTY2 has an effect of inhibiting Beta amyloid and a hyperphosphorylated neuronal micro-tubule-associated protein (Tau protein), without affecting the development of nerve cells and having the ability to promote the growth of the nerve cells; and the two types of proteins have a crucial impact on the neurodegenerative diseases.

2 Claims, 9 Drawing Sheets

HIGH-EXPRESSION TYPE MESENCHYMAL STEM CELLS, CULTURE METHOD AND USE THEREOF

CROSS-REFERENCE TO RELATED APPLICATION

The present application claims priority from Taiwanese Patent Application No. 111122945 filed on Jun. 21, 2022, the contents of which are incorporated herein by reference in their entirety.

BACKGROUND OF THE INVENTION

1. Field of the Invention

The present invention relates to the technical field of treatment for neurodegenerative diseases, and in particular to high-expression type mesenchymal stem cells capable of highly expressing LEFTY2 (Left-Right Determination Factor 2), a culture method and use thereof.

2. Description of the Related Art

Dementia is divided into lots of major types. Alzheimer's disease is one of the most common dementia types, and its main pathological feature is accumulation of Beta amyloid while its obvious symptom is short-term memory decline. FTLD (Frontotemporal Lobar Degeneration) is a degenerative brain disease characterized by gradual atrophy in the frontal lobe and temporal lobe of the brain. It is another major type of dementia, and is also called aphasia type dementia because its degeneration starts from verbal communication. A difference from Alzheimer's disease is that FTLD does not necessarily involve the accumulation of Beta amyloid, but is obviously associated with hyperphosphorylation of the Tau protein.

Dementia will lead to intracellular neurofibrillary tangles, synaptic dysfunction and symptoms of inflammation in the brain. Lots of stem cells are now available for treating dementia and have many functions of inflammation resistance, regeneration of the blood vessels of the brain, protection and regeneration of brain cells, etc. These cells can secrete growth factors to enhance proliferation of endogenous neural stem cells. Previous studies have shown that ADSCs (Adipose-Derived Stem Cells) can interact with the cultured neural stem cells and significantly support their proliferation and survival, and a physical contact between the two types of cells is deemed essential to inducing neuronal differentiation.

Adipose cell-free derivatives have recently attracted attention as potential therapeutic agents for various human diseases. Recent studies have indicated that the proliferation of ADSCs-conditioned medium, paracrine cytokines, exosomes and other active substances is a major factor enabling the ADSCs to play their biological role. However, given the complex content of the adipose cell-free derivatives, the key is to find out which kind of proteins regulates the ADSCs, and to secrete such kind of proteins to produce an effect of treating dementia.

SUMMARY OF THE INVENTION

In view of this, an objective of the present invention is to provide a medicine for treating neurodegenerative diseases, which employs LEFTY2 (Left-Right Determination Factor 2) generated by co-culturing mesenchymal stem cells with neural stem cells, and does not require a direct contact between the mesenchymal stem cells and the neural stem cells in the culture process. The LEFTY2 has an effect of inhibiting Beta amyloid and a hyperphosphorylated neuronal microtubule-associated protein (Tau protein), without affecting the development of nerve cells and having the ability to promote the growth of the nerve cells; and the two types of proteins have a crucial impact on the neurodegenerative diseases.

Specifically, the present invention provides a method for culturing high-expression type mesenchymal stem cells, by co-culturing initial mesenchymal stem cells with nerve cells in a first medium for 24 to 196 h, wherein the initial mesenchymal stem cells can be procured from different sources including adipose tissue, dental pulp, bone marrow tissue and umbilical cord tissue of mammals; the first medium is a Neurobasal medium comprises B-27 Supplement, N-2 Supplement, L-glutamine, non-essential amino acids, penicillin/streptomycin and heparin; the nerve cells have mutations in the APP (Amyloid precursor protein) gene; and the mesenchymal stem cells can highly express LEFTY2.

In an embodiment of the present invention, a ratio of the number of the initial mesenchymal stem cells to the number of the nerve cells is between 1:0.01 and 1:100.

In an embodiment of the present invention, the nerve cells are induced pluripotent stem cells produced by reprogramming the somatic cells of a dementia patient, or nerve cells obtained after differentiation of an induced pluripotent stem cell with Trisomy 21.

In an embodiment of the present invention, the above-mentioned culturing method can further comprise: collecting the first medium after the co-culture and performing filtration and concentration to obtain a protein complex, the protein complex comprising at least one of Thrombospondin-1, Galectin-7, Alpha-2-HS-glycoprotein, Sparc protein, Keratin type II cytoskeletal 74, Nucleophosmin and FSTL1 protein (Follistatin-related protein 1).

Also, the present invention can provide another method for culturing high-expression type mesenchymal stem cells, by co-culturing initial mesenchymal stem cells with a first specific protein in a second medium for 24 to 196 h, wherein the initial mesenchymal stem cells are from mammals; the second medium is a Neurobasal medium comprises at least one of B-27 Supplement, N-2 Supplement, L-glutamine, non-essential amino acids, penicillin/streptomycin, and heparin; the first specific protein is at least one of Thrombospondin-1, Galectin-7, Alpha-2-HS-glycoprotein, Sparc protein, Keratin type II cytoskeletal 74, Nucleophosmin and FSTL1 protein; and the mesenchymal stem cells can highly express LEFTY2.

In an embodiment of the present invention, when the number of the initial mesenchymal stem cells is set as X1 and the concentration of the first specific protein in the second medium is set as Y1 ng/mL, a ratio of X1 to Y1 is between $1\times10^6{:}10$ and $1\times10^6{:}1,000$.

In addition, the present invention can also provide high-expression type mesenchymal stem cells, which are mesenchymal stem cells prepared by the above-mentioned culturing method and capable of highly expressing LEFTY2.

Furthermore, the present invention also provides a method for producing LEFTY2, comprising the following steps: a step of co-culturing: initial mesenchymal stem cells are co-cultured with nerve cells in a first medium, or the initial mesenchymal stem cells are co-cultured with a first specific protein in a second medium; and a step of collecting a finished product: a cell culture solution obtained in the culture process, or high-expression type mesenchymal stem cells obtained in the step of co-culturing are extracted, to obtain LEFTY2; wherein the animal mesenchymal stem cells are any one of adipose tissue, dental pulp of deciduous teeth, myeloid tissue and umbilical cord tissue of mammals; the first medium and the second medium each is a Neurobasal medium comprise B-27 Supplement, N-2 Supplement, L-glutamine, non-essential amino acids, penicillin/streptomycin, and heparin; the nerve cells have mutations in the APP gene; the first specific protein is at least one of Thrombospondin-1, Galectin-7, Alpha-2-HS-glycoprotein, Sparc protein, Keratin type II cytoskeletal 74, Nucleophosmin and FSTL1 protein; and the high-expression type mesenchymal stem cells can highly express LEFTY2.

Also, the present invention provides a pharmaceutical composition for treating a neurodegenerative disease, at least comprising LEFTY2 and/or the above-mentioned high-expression type mesenchymal stem cells.

In an embodiment of the present invention, in the pharmaceutical composition, the concentration of the LEFTY2 is greater than 25 ng/mg.

In an embodiment of the present invention, the neurodegenerative disease is FTLD (Frontotemporal Lobar Degeneration), Alzheimer's disease, or amyloidosis.

Hereinafter, one or more embodiments of the present invention are described in detail. The above-mentioned characteristics of the present invention will be clearer through the following detailed description and the attached claims. It should be understood that the above general description and the following detailed description are only for an illustrative purpose and thus are exemplary, with no intention of limiting the scope of the present invention.

DETAILED DESCRIPTION OF THE PREFERRED EMBODIMENTS

Figure 1A:
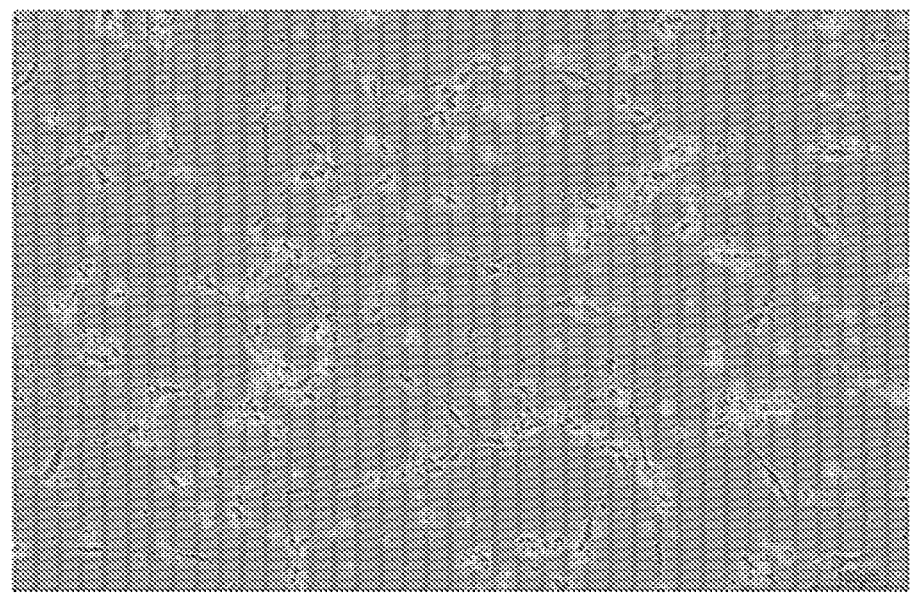
FIG. 1A and FIG. 1B respectively illustrate the cell appearance images (at a magnification of 100×) of APP over neurons cultured alone and co-cultured with ADSCs.

Hereinafter, the implementation modes of the present invention are elaborated and described in a more detailed way by listing different specific embodiments, so as to make the spirit and content of the present invention more complete for easier understanding. However, those of common knowledge in the art shall understand that the present invention is certainly not limited to these embodiments, and the present invention can also be made by use of other same or equivalent functions and orders of steps.

All technical and scientific terms used herein have the same meanings as those generally understood by those of common skill in the field of the present invention. In addition, unless otherwise contradicted undoubtedly in the context, a singular term used herein shall include its plural form, and a plural term shall include its singular form.

Unless otherwise defined herein, the term "treat/treating/treatment" means an act of delivery to a patient suffering from a specific disease or symptom, where the act can alleviate the disease or symptom of the patient, or reduce the severity of one or more symptoms, or slow down or delay the progression of the disease or symptom.

Herein, the term "individual" or "patient" can be exchanged with each other. The term "individual" or "patient" refers to an animal which can be treated using a compound and/or a method respectively, including, but not limited to, dogs, cats, horses, sheep, pigs, cows and similar animals as well as humans and non-human primate animals. Unless otherwise specified, the "individual" or "patient" may include males and females. In addition, it also includes the individuals or patients receiving treatment using the pharmaceutical composition and/or method of the present invention.

Although the numerical ranges and parameters for describing the wide scope of the present invention are approximate values, the numerical values described in a specific example shall be reported as accurately as possible. However, any numerical value itself includes some errors inevitably caused by a standard deviation present in respective test and measurement. Herein, the term "about" generally means that the actual value is within 10%, 5%, 1% or 0.5% greater than or less than a specific value or range. Alternatively, the term "about" means that the actual value falls within an acceptable standard deviation of the average when considered by those of common skill in the art. Unless in an example or otherwise clearly indicated, all ranges, quantities, values and percentages (e.g., quantity for describing a material, time, temperature, operating conditions, quantity ratio and the like) used herein shall be understood as being modified by the term "about". Therefore, unless specified on the contrary, the numerical parameters revealed in this specification and the attached claims are all approximate values, and may be changed if necessary. In any case, each numerical parameter shall at least comply with the numerical value with significant digits as reported and be explained using the common rounding technique.

In an implementation mode of the present invention, the present invention provides a method for culturing high-expression type mesenchymal stem cells, by using mesenchymal stem cells from mammals as initial mesenchymal stem cells and co-culturing with nerve cells having mutations in the APP gene. The culture time is generally between 24 h and 196 h, preferably between 48 h and 144 h, and most preferably between 74 h and 120 h.

The MSCs (Mesenchymal Stem Cells) used in the present invention belong to pluripotent stem cells and can be differentiated into different types of cells, including adipose cells, bone cells, cartilage cells, etc. Also, the tissue source of the mesenchymal stem cells includes, but is not limited to, any one of adipose tissue, dental pulp of deciduous teeth, myeloid tissue and umbilical cord tissue, and preferably the adipose tissue or myeloid tissue.

The mesenchymal stem cells obtained by the co-culture have a characteristic of highly expressing LEFTY2 (Left-Right Determination Factor 2); and specifically, the LEFTY2 content in the mesenchymal stem cells is increased by more than 3 times over the initial mesenchymal stem cells, preferably by more than 30 times.

From the above description, the co-culture mode may be direct culture or indirect culture. In the direct culture mode, the initial mesenchymal stem cells and the nerve cells having mutations in the APP gene are placed in the same culture dish for culturing, and in the co-culture mode, there is no direct contact between the initial mesenchymal stem cells and the nerve cells having mutations in the APP gene, and the two can be separated by a permeable film support disposed therebetween, e.g., a PET film. In addition, the composition of the medium used for the co-culture is a Neurobasal medium includes 0.5-2 wt % of B-27 Supplement, 0.5-2 wt % of N-2 Supplement, 0.5-2 wt % of L-glutamine, 0.5-2 wt % of NEAA (Non-essential amino acids), 0.5-2 wt % of a P/S (Penicillin-Streptomycin) solution, and 0.5-2 µg/mL of Heparin, but is not limited thereto; and the medium can further include G-5 Supplement, SB431542, 2-Mercaptoethanol or FGF-2. In addition, a High-glucose DMEM medium or a DMEM-F12 medium can also be used as a basal medium.

According to the technical idea of the present invention, during the co-culture, a ratio of the number of the initial mesenchymal stem cells to the number of the nerve cells having mutations in the APP gene is between 1:0.01 and 1:100, preferably between 1:0.5 and 1:50, more preferably between 1:0.1 and 1:10, and most preferably between 1:1 and 1:5.

Besides, in other embodiments of the present invention, Thrombospondin-1 (TSP-1) can also be added into the medium and co-cultured with the mesenchymal stem cells to obtain high-expression type mesenchymal stem cells for highly expressing LEFTY2. The culture time is generally between 24 h and 196 h, preferably between 48 h and 144 h, and most preferably between 74 h and 120 h.

From the above description, when the number of the initial mesenchymal stem cells is set as X1 and the concentration of the TSP-1 in the second medium is set as Y1 ng/mL, a ratio of X1 to Y1 is generally between $1 \times 10^6:10$ and $1 \times 10^6:1,000$, preferably between $1 \times 10^6:50$ and $1 \times 10^6:800$, more preferably between $1 \times 10^6:100$ and $1 \times 10^6:500$, and most preferably between $1 \times 10^6:150$ and $1 \times 10^6:300$.

The mesenchymal stem cells after the co-culture are collected and subjected to cell extraction to obtain LEFTY2; and the first medium or the second medium obtained in the culture process is also rich in LEFTY2, and thus a culture solution obtained in the culture process can also be collected, and LEFTY2 is extracted therefrom.

According to the technical idea of the present invention, both the high-expression type mesenchymal stem cells for highly expressing LEFTY2 and the LEFTY2 can be used as a component of a pharmaceutical composition for treating a neurodegenerative disease, and are key proteins helping the nerve cells with dementia symptoms survive.

From the above description, in the pharmaceutical composition, the content of LEFTY2 is generally greater than 25 ng/mL, preferably between 25 ng/mL and 1,000 ng/mL, more preferably between 50 ng/mL and 1,000 ng/mL, and most preferably between 100 ng/mL and 1,000 ng/mL.

According to the above description, the revealed pharmaceutical composition can be prepared by a well-known medicine preparation procedure. In an implementation mode of the present invention, the pharmaceutical composition revealed in the present invention can be delivered through any proper administration route, for example, through oral administration via capsules, suspension or lozenges, or in a systemic delivery mode for parenteral delivery via intramuscular injection, intravenous injection, subcutaneous injection or intraperitoneal injection. In addition, in some embodiments, the pharmaceutical composition revealed in the present invention can also be delivered through a transmucosal or transdermal way, for example, topical skin application, or bronchial, nasal or oral inhalation, or instillation as nasal drops; and can also be delivered through the recta.

Similarly, in the present invention, a pharmaceutically acceptable excipient means an excipient compatible with other components of a pharmaceutical preparation and compatible with an organism, for example, an encapsulating material or various additives such as an absorption enhancer, an antioxidant, an adhesive, a buffer solution, a coating agent, a colorant, a diluent, a disintegrant, an emulsifier, a supplement, a filling agent, a flavoring agent, a humectant, a lubricant, a spice, a preservative, a propellant, a release agent, a bactericide, a sweetener, a solubilizer, a wetting agent and a mixture thereof.

Similarly, in other embodiments, a liquid preparation containing the pharmaceutical composition of the present invention is made into a sterile injectable solution or suspension, for example, a solution suitable for delivery via intravenous, intramuscular, subcutaneous or intraperitoneal injection.

For more comprehensive and complete description of the present invention, the implementation modes and specific examples of the present invention are illustratively described below, which, however, does not represent an intention of a unique practical or usable form in the specific examples of the present invention. The embodiments cover the characteristics and structures of a plurality of specific examples, as well as the process steps and orders for operating these specific examples. However, other examples can be implemented through the same or equivalent functions and order of steps.

First, a standard operation process for testing in the examples of the present invention is described.

Western Blot

Protein extraction and a Western blot test were included; and total protein was extracted and collected and stored at −80° C. In the Western blot test, the extracted proteins were mixed with a 3× protein binding agent; and the mixture was heated to 100° C. for about 15 min, and then placed on ice for about 1 min. Protein electrophoresis was performed using 10% SDS-PAGE, and the voltage was set to 90 V for about 1 h. Transfection was performed using a PVDF film at 100 V for about 2 h, which was hindered using 5% low-fat milk for 1 h. A first antibody was added into a refrigerator at 4° C. till next day. The PVDF was taken out and then rinsed 3 times using a buffer solution, 10 min each time. A second antibody was added and allowed to stand at room temperature for 1 h, and then washed 3 times using TBS-T, 10 min each time. The resulting product was allowed to react with an enzyme luminescent reagent for 1 min, and then pressed using a photosensitive film. After that, scanning and quantifying were performed.

Immunofluorescent Staining

Cells were cultured onto a glass slide, and after growing into a single layer, washed twice using PBS. The cells were fixed using 4% paraformaldehyde. Holes were poked in the cell membranes using Triton-X-100. The cells were sealed using 5% FBS, generally for 30 min. Reactions were allowed at room temperature for 1 h or at 4° C. overnight. The resulting product was washed using PBS-T. Two antibodies were needed for indirect immunofluorescence. Reactions were allowed at room temperature for 1 h in darkness. The resulting product was flushed with PBS-T. Nuclear staining was performed using DAPI, and a fluorescence microscope was used for examination.

Real-time polymerase chain reaction Before a real-time polymerase chain reaction, a test body was prepared, the concentration of cDNA was quantitatively determined, and the concentration of each tube was adjusted to 50 μg or 100 μg. 2 μl of cDNA, 5.5 μL of nuclease-free water and 0.5 μL of SYBR Green were added into the same centrifuge tube. After 5 min of centrifugation at 1,500 rpm, analysis was performed using a Roch LightCycler 480 system instrument.

Hereafter, the present invention will be described in detail through preferred embodiments of the present invention.

Culture of Nerve Cells

In the present invention, nerve cells were obtained by differentiating an induced pluripotent stem cell (AD-iPSC) produced from the blood cells of a patient with dementia (Alzheimer's disease) by using a retrovirus, or an induced pluripotent stem cell (Ts-21-iPSC) with Trisomy 21. The Ts-21-iPSC has excessive expression of APP (Amyloid precursor protein), while the AD-iPSC has mutations in the APP gene. The two types of cells can be differentiated into nerve cells while producing Beta amyloid deposition and Tau protein phosphorylation.

After the cells containing excessive expression of the APP gene were treated using a cell isolation reagent Accutase (A11105-01, Gibco), the cells containing excessive expression of the APP gene were subjected to suspension culture in a DMEM/F12 medium (11330-032, Gibco), 1 wt % of L-glutamine (25030-081, Gibco), 1 wt % of non-essential amino acids (11140-050, Gibco), 0.1 wt % of 2-mercapto-ethanol (21985-023, Gibco) and 1 wt % of a penicillin/streptomycin solution (15140-122, Gibco) were added to 20 wt % of a serum substitute (10828-028, Gibco), and embryoid bodies were accumulated and cultured. The medium for induction culture of nerve cells was changed every other day.

The embryoid bodies were grown in a neural induction medium in which a high-glucose DMEM medium (11965092, Gibco) was mixed with a DMEM-F12 medium (12660012, Gibco) and 1% of L-glutamine (25030-081, Gibco) was added. The neural induction medium contained 1% of non-essential amino acids (11140-050, Gibco), 1% of a penicillin/streptomycin solution (15140-122, Gibco), 1 μg/mL heparin (H3149, Sigma), 0.5 μM BIO (B1686, Sigma), 10 μM SB431542 (S4317, Sigma) and 10 ng/mL FGF-2 (F0291, Sigma). After two consecutive days of cell culture, the medium was changed into a neurobasal medium.

The neurobasal medium was a Neurobasal medium (21103-044, Gibco) containing 1 wt % of B-27 Supplement (17504-044, Gibco), 1 wt % of N-2 Supplement (17502-048, Gibco), 1 wt % of L-glutamine (25030-081, Gibco), 1 wt % of non-essential amino acids (11140-050, Gibco), 1 wt % of a penicillin/streptomycin solution (15140-122, Gibco), and 1 μg/mL heparin (H3149, Sigma). The medium was changed every two days. After the cells were attached to a culture dish for several days, neurons could be observed, which took about 30 days or more, and then neurons having excessive expression of APP (Amyloid precursor protein) gene (hereinafter referred to as APP over neurons) were obtained.

Co-Culture of Neurons Using Adipose-Derived Stem Cells

The mesenchymal stem cells used in this embodiment are ADSCs (Adipose-Derived Stem Cells) present in adipose tissue, and can be obtained easily by liposuction or lipectomy while causing few traumas to the patient. In addition, the ADSCs can be implanted after extraction, which is easily accepted by the patient and reduces the shortcomings such as anti-rejection drugs and long-time in-vitro culture. Furthermore, it is easy to isolate a mass of ADSCs, and the ADSCs can be proliferated rapidly and stably during in-vitro culture and are not prone to aging, thereby being applicable to the present invention.

A high-glucose DMEM medium (11965092, Gibco) was mixed with 1% of matrigel (354230, Corning) to form a new matrigel which was coated in a 6-well culture plate (3516, Costar); 30 min later, the matrigel was removed, and $5 \times 10^5$ APP over neurons were inoculated in the 6-well culture plate, then $5 \times 10^4$ ADSCs were inoculated into a 100 nm culture inlay plate (353093, Falcon) and inlaid into a 6-well culture plate containing neurons and cultured; upper-layer cells were ADSCs, and the lower-layer cells were APP over neurons; the medium used has the same composition as the above-mentioned neurobasal medium; and the medium solution could exist in both the 6-well culture plate and the culture inlay plate through a permeable film at the bottom of the culture inlay plate.

Figure 1B:
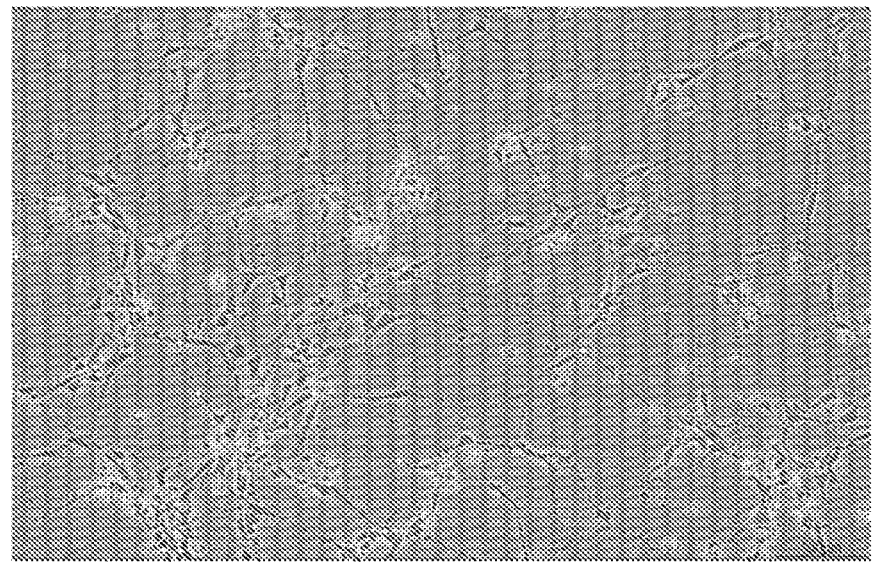

After 72 h of culture, the cell appearances of APP over neurons when cultured alone and when co-cultured with ADSCs were observed using a fluorescence microscope by means of immunofluorescent staining. As shown in FIG. 1A and FIG. 1B, the APP over neurons, when cultured alone, show short cell morphology and axonal expression as well as few neural connection networks (FIG. 1A); and by contrast, the APP over neurons, after being co-cultured with ADSCs, show long cell morphology and axonal expression as well as many neural connection networks (FIG. 1B).

In addition, the number of cells proliferated under the same number ($1 \times 10^6$) of the APP over neurons and the same culture time (48 h) was calculated. The number of the cells proliferated after the APP over neurons were cultured alone for 48 h was $8 \times 10^5$, and the number of the cells proliferated after the APP over neurons were co-cultured with ADSCs was $1.1 \times 10^6$, indicating that after co-culture with ADSCs, the number of APP over neurons is significantly increased.

Analysis of Exosomes

Exosomes are part of extracellular vesicles, with a dimension of about 30 nm to 100 nm. A culture solution after the ADSCs were co-cultured with the APP over neurons was collected, the nanoparticles with about the same dimension in the cell culture solution were tested using a nanoparticle tracking analyzer (NanoSight NS300), and then the dimension and concentration of the particles were analyzed and compared with a control group (APP over neurons cultured alone), with the results recorded in Table 1.

TABLE 1

|  | | Control group | Co-culture group |
|---|---|---|---|
| Exosome | Average diameter (nm) | 135.8 ± 2.9 | 159.2 ± 2.0 |
|  | Concentration (particle number/mL) | $2.84e^{+09} \pm 9.62e^{+07}$ | $3.78e^{+09} \pm 1.71e^{+07}$ |

It can be seen from the results of the above Table 1 that the volume and number of exosomes are significantly increased when the APP over neurons are co-cultured with the ADSCs.

Content Analysis of LEFTY2 Proteins

The expression quantity of LEFTY2 proteins in the culture solution after the ADSCs were co-cultured with the APP over neurons was analyzed using a high-performance liquid chromatography instrument (Thermo, UHPLC 3000), and differences between the control group (APP over neurons cultured alone) and the co-culture group (APP over neurons co-cultured with ADSCs) were analyzed, with the results shown in Table 2 below.

TABLE 2

|  | Control group | Co-culture group |
|---|---|---|
| LEFTY2 protein | 0% | 100% |

By testing the culture solution after the APP over neurons were co-cultured with ADSCs (co-culture group), it was found that LEFTY2 expression is significantly increased while there was no LEFTY2 in the APP over neurons not co-cultured with ADSCs (control group).

Figure 2:
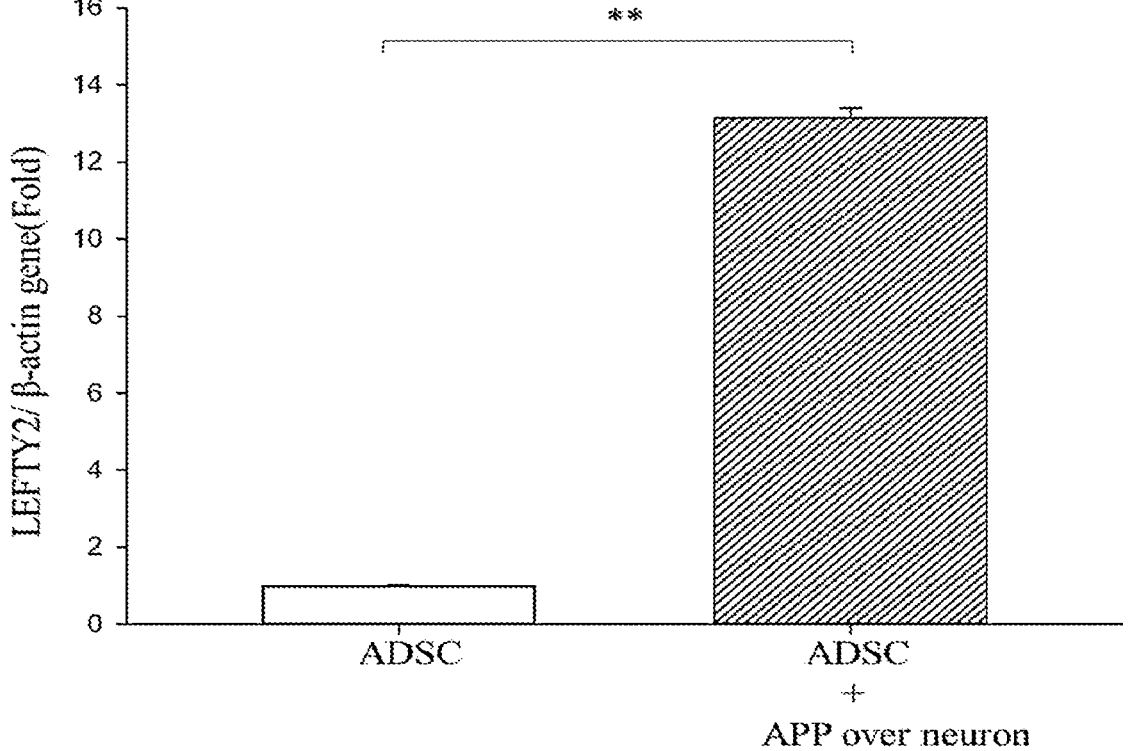
FIG. 2 is a comparison diagram illustrating the expression quantity of LEFTY2 gene in a control group (ADSC) and a co-culture group (ADSC+APP) during the content analysis of LEFTY2 proteins.

In addition, the expression quantities of LEFTY2 gene in the ADSCs cultured alone and in the ADSCs of the co-culture group were analyzed using Western blot. As shown in FIG. 2, the LEFTY2 gene in the co-culture group was expressed in large quantities, which is 13 times the expression quantity of the LEFTY2 gene in the ADSCs cultured alone. So, it can be confirmed that lots of LEFTY2 genes can be produced after ADSCs are co-cultured with APP over neurons.

Proteomics Analysis

The medium for culturing APP over neurons alone (control group) and the medium for co-culturing ADSCs with APP over neurons (co-culture group) were taken out respectively and subjected to proteomics identification. After the collected medium liquid was filtered using a 0.2 μm filter, proteins were further concentrated using a centrifugal filter (Amicon Ultra Centrifugal filters, Millipore, USA), and stored at −80° C. for further analysis.

The concentrated proteins were hydrolyzed using Trypsin into small pieces of peptide fragments, and proteomics analysis was performed using high-resolution LC-MS/MS, where the instrument used was LTQ-Orbitrap Velos hybrid mass spectrometer equipped with a PicoView nano spray interface (Thermo Scientific). After the fragments with poor hydrophobicity were separated, each peptide fragment was analyzed using a mass spectrometer, and the peptide fragments were separated from each other according to different values of their charge-mass ratios, to obtain a first-level mass spectrum. The high-peak peptide fragments were further fragmented into smaller peptide fragments. The peptide fragments selecting collision-induced dissociation of isotopes were separated into y- or b-ions, and these ions were isolated using a second-level mass spectrometer. By calculating mass differences between adjacent y- or b-ions, amino acids and peptide sequences of different masses could be obtained. The results are shown in Table 3.

TABLE 3

|  | Control group | Co-culture group |
|---|---|---|
| Thrombospondin-1 | 0% | 200% |
| Galectin-7 | 25.5 pg | 174.5 pg |
| Alpha-2-HS-glycoprotein | 25.7 pg | 164.4 pg |
| Sparc protein | 35.6 pg | 159.4 pg |
| Keratin type II cytoskeletal 74 | 40.6 pg | 174.3 pg |
| Nucleophosmin | 48.3 pg | 151.7 pg |
| FSTL1 protein (Follistatin-related protein 1) | 46.6 pg | 153.4 pg |

It can be seen from the above Table 3 that, by testing the culture solution after the APP over neurons were co-cultured with ADSCs (co-culture group), it was found that the expression of TSP-1 (Thrombospondin-1) is significantly increased while there is no TSP-1 in the culture solution of the APP over neurons not co-cultured with ADSCs (control group); and the contents of other proteins such as Galectin-7, Alpha-2-HS-glycoprotein, Sparc protein, Keratin type II cytoskeletal 74, Nucleophosmin and FSTL1 protein (Follistatin-related protein 1) are also significantly increased.

According to the literature, TSP-1 (Thrombospondin-1) can prevent Aβ-induced mitochondrial rupture and dysfunction in hippocampal cells; Alpha-2-HS-glycoprotein has a potential for a neuroprotective effect; Sparc protein can assist in the neuronal health and recovery after injuries of the central nervous system; NMP (Nucleophosmin) has the potential for treating neurodegenerative diseases, indicating that lots of components effective in treating neurodegenerative diseases can be produced after ADSCs are co-cultured with APP over neurons.

Co-culture of TSP-1 with ADSCs TSP-1 at a concentration of 200 ng/mL was added to a Neurobasal medium (21103-049, Gibco) containing 1% of B-27 Supplement, 1 wt % of N-2 Supplement, 1 wt % of L-glutamine (25030-081, Gibco), 1 wt % of non-essential amino acids (11140-050, Gibco), 1 wt % of a penicillin/streptomycin solution (15140-122, Gibco) and 1 μg/mL heparin (H3149, Sigma), and $1 \times 10^6$ ADSCs were inoculated into a 6-well culture plate and cultured using the above-mentioned medium; after 48 h of culture, analysis was performed through a real-time polymerase chain reaction to confirm the gene expression quantities of LEFTY2 in the group of ADSCs with TSP-1 and the group of ADSCs without TSP-1.

Figure 3:
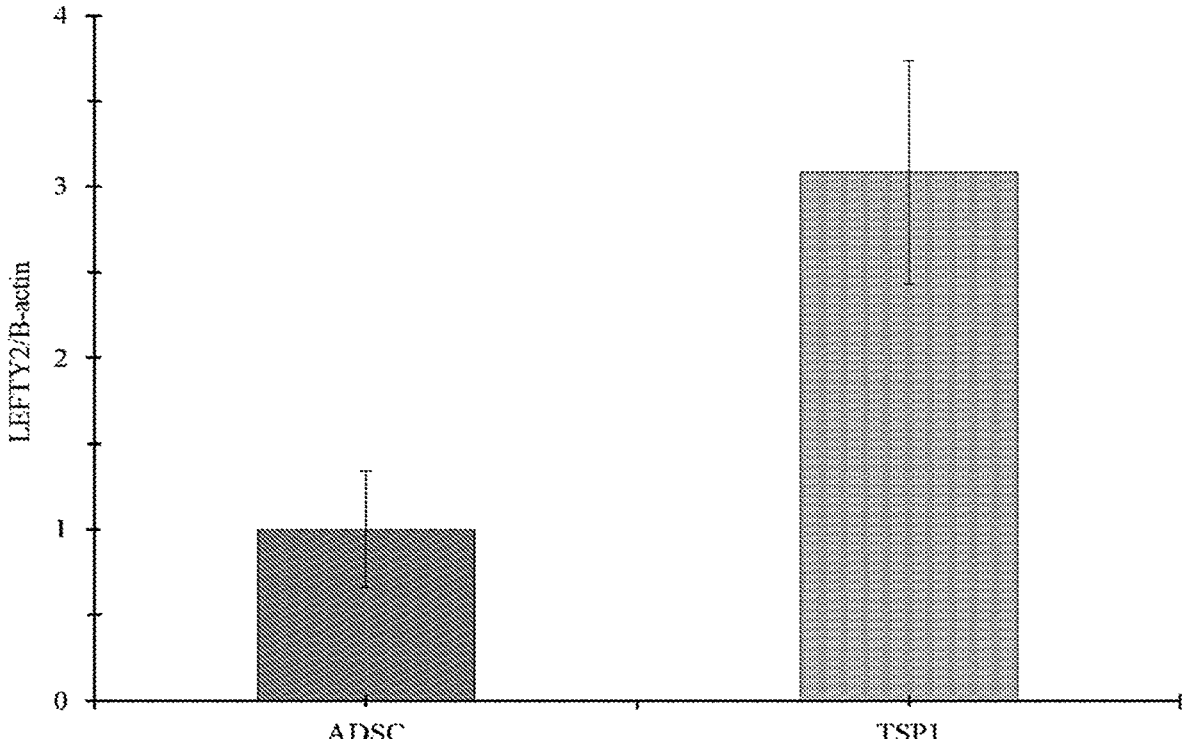
FIG. 3 is a comparison diagram illustrating the expression quantity of LEFTY2 gene in a control group (ADSC) and TSP-1 group during the expression analysis of LEFTY2 gene.

It can be seen from the results of FIG. 3 that, the LEFTY2 gene in the co-culture group is expressed in large quantities, which is 3.08 times the expression quantity of LEFTY2 in the group of ADSCs with TSP-1; and it can be confirmed that a large quantity of LEFTY2 can also be produced after ADSCs are co-cultured with TSP-1.

Inhibition Analysis of LEFTY2 Against Biomarkers of Neurodegenerative Diseases

Figure 8:
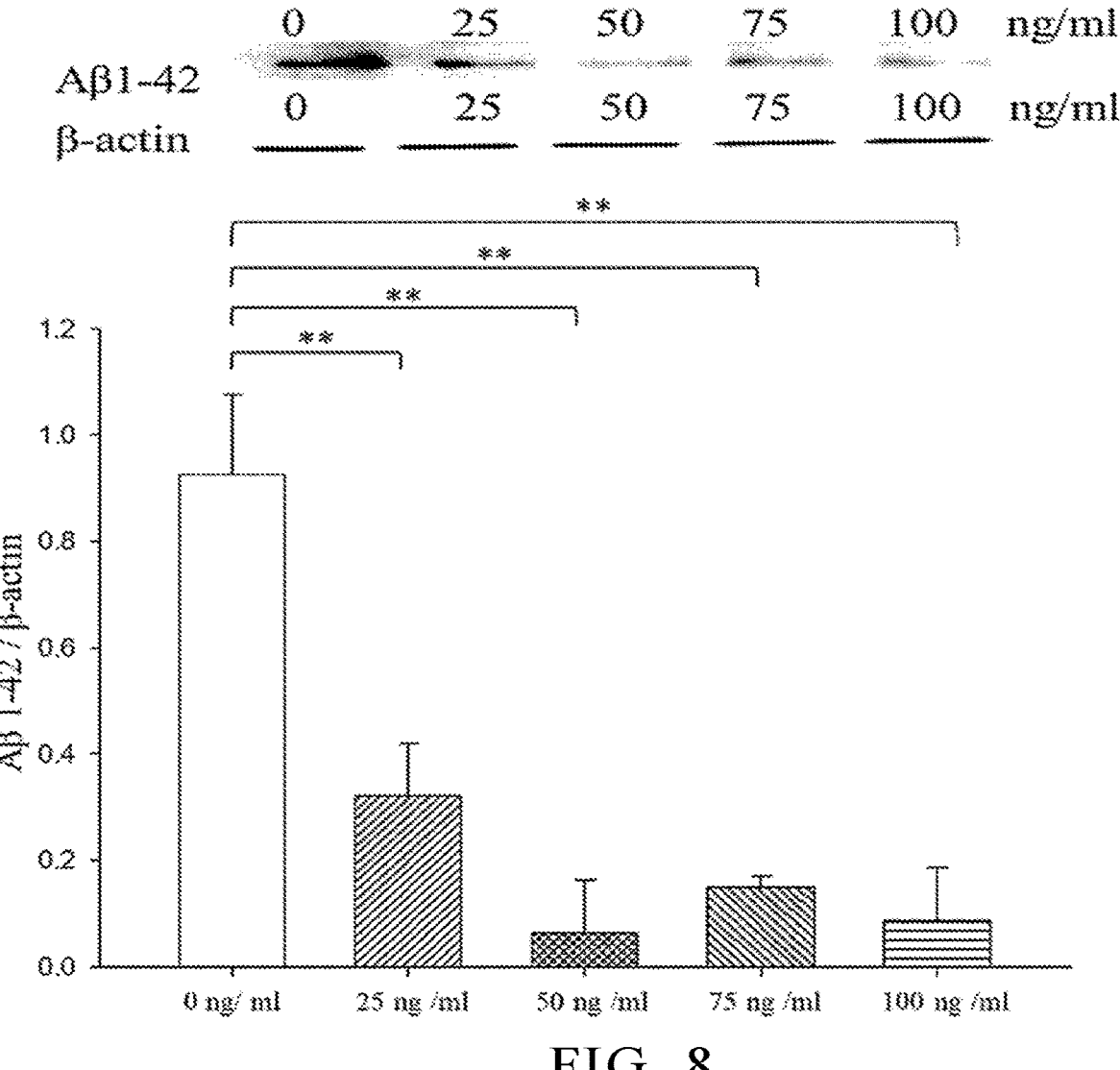
FIG. 8 is a comparison diagram illustrating the expression quantity of amyloid $A\beta1\text{-}42$ in each group of APP over neurons under the treatment using LEFTY2 at different concentrations during inhibition analysis of amyloid $A\beta1\text{-}42$.
Figure 9:
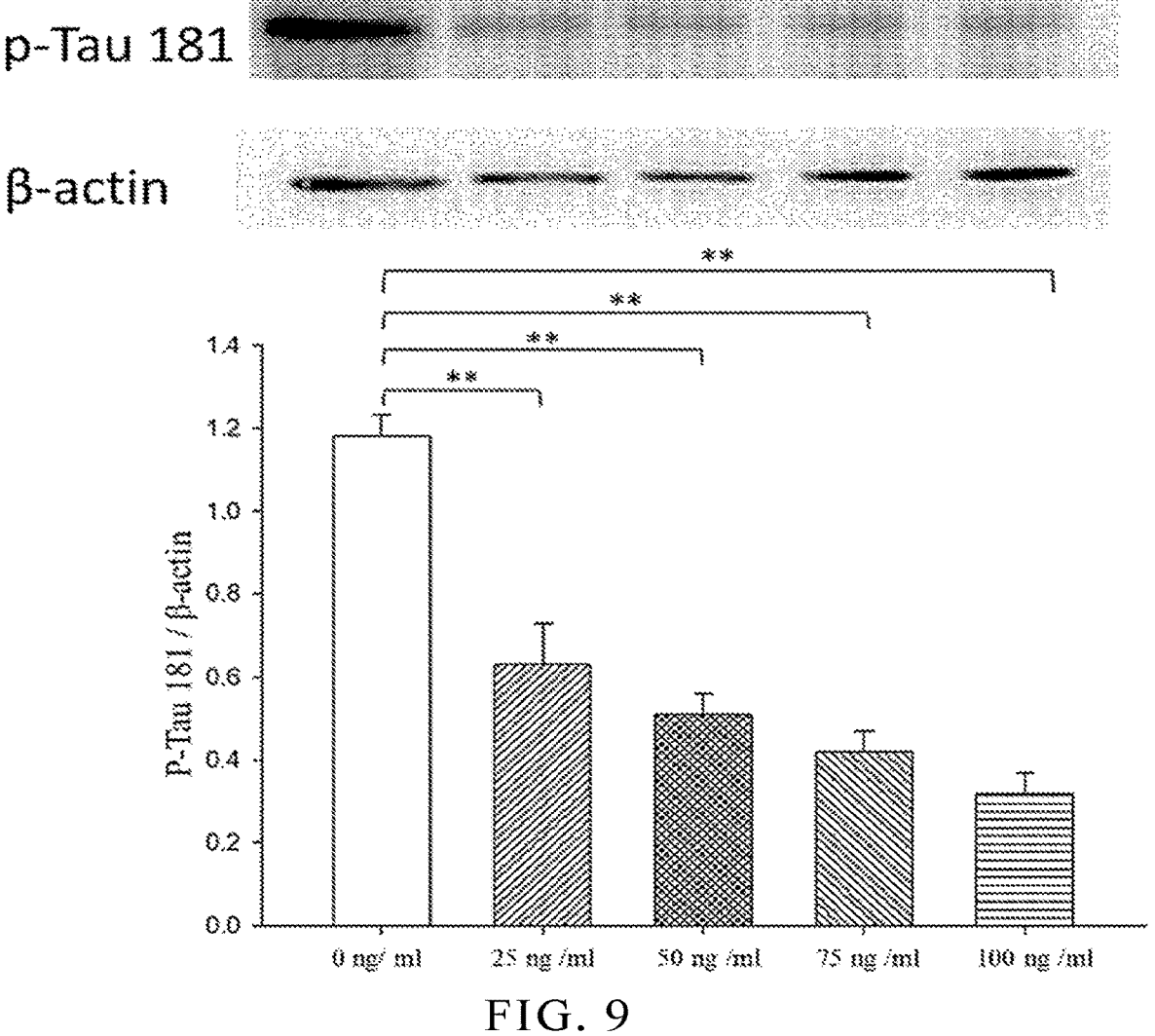
FIG. 9 is a comparison diagram illustrating the expression quantity of p-Tau181 protein in each group of APP over neurons under the treatment using LEFTY2 at different concentrations during inhibition analysis of p-Tau181 protein.

LEFTY2 at different concentrations (0 ng/mL, 25 ng/mL, 50 ng/mL, 75 ng/mL and 100 ng/mL) were respectively added to APP over neurons (at a cell concentration of $1 \times 10^6$/mL); after 2 days of culture, the gene expression quantities of APP, Aβ1-42 and p-Tau181 in each group of APP over neurons were analyzed through a real-time polymerase chain reaction. The results are recorded in Table 4 and respectively drawn as FIG. 4, FIG. 8 and FIG. 9.

TABLE 4

| Name (unit) | Group 1 | Group 2 | Group 3 | Group 4 | Group 5 |
|---|---|---|---|---|---|
| LEFTY2 (ng/mL) | 0 | 25 | 50 | 75 | 100 |
| APP/β-actin (times) | 1 | 0.2 | 0.3 | 0.25 | 0.48 |
| Aβ1-42/β-actin (times) | 1 | 0.3 | 0.05 | 0.2 | 0.08 |
| p-tau181/β-actin (times) | 1.1 | 0.58 | 0.48 | 0.39 | 0.27 |

Figure 4:
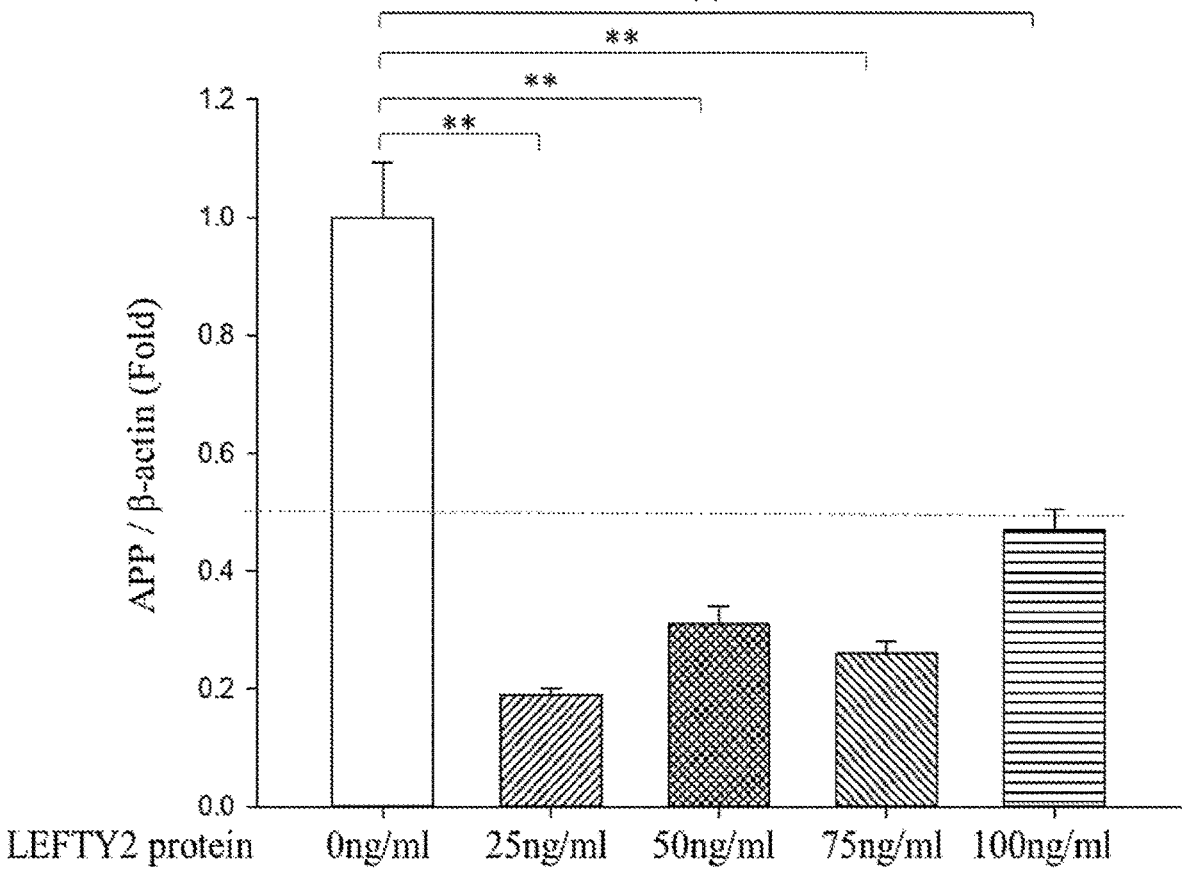
FIG. 4 is a comparison diagram illustrating the expression quantity of APP gene in each group of APP over neurons under the treatment using LEFTY2 at different concentrations during the inhibition analysis of APP gene.

It can be seen from the results shown in Table 4 and FIG. 4 that, compared with the group (group 1) without LEFTY2, the APP gene in the group with LEFTY2 is significantly reduced to less than 0.5 times, indicating that LEFTY2 can effectively inhibit the APP gene.

Figure 5:
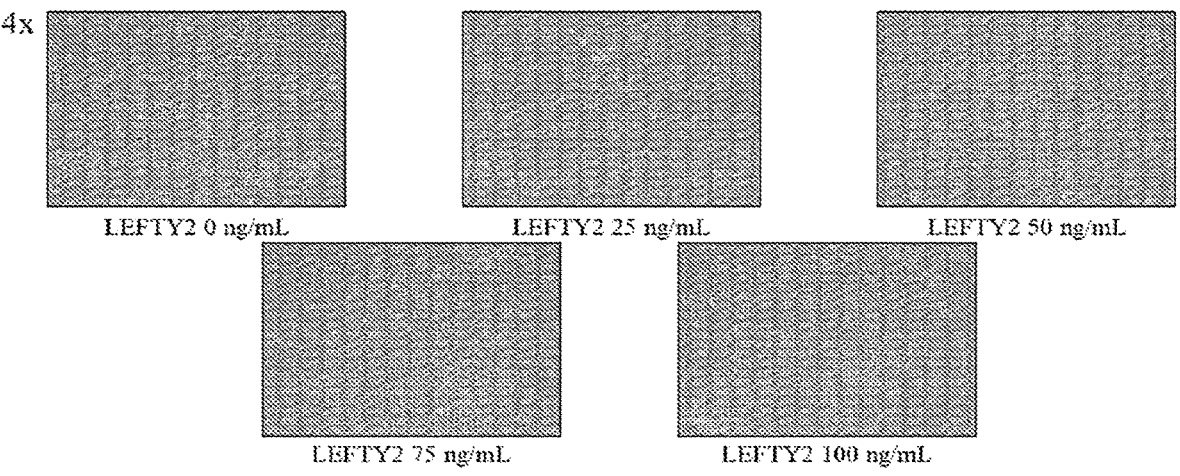
FIG. 5 illustrates the microscopic images, at a magnification of 4, of each group of APP over neurons under the treatment using LEFTY2 at different concentrations.
Figure 6:
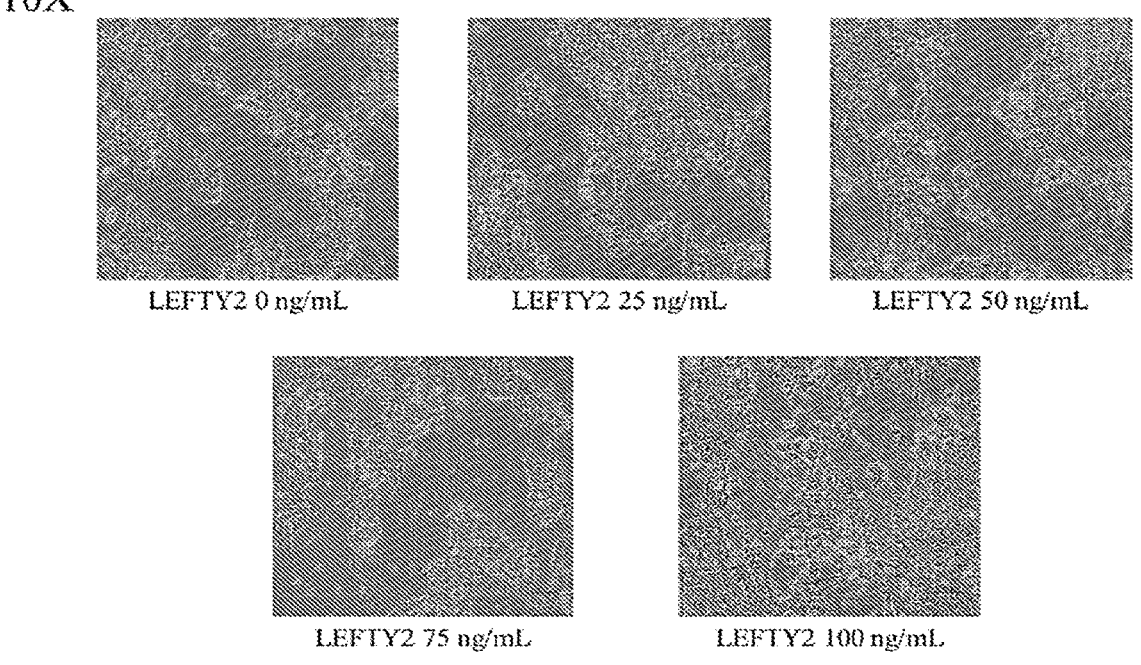
FIG. 6 illustrates the microscopic images, at a magnification of 10, of each group of APP over neurons under the treatment using LEFTY2 at different concentrations.

In addition, the cell morphology and number of APP over neurons in the groups with LEFTY2 at different concentrations were observed using a microscope. Referring to FIG. 5 and FIG. 6, FIG. 5 illustrates the microscopic images, at a magnification of 4, of APP over neurons in the groups with LEFTY2 at different concentrations, and FIG. 6 illustrates the microscopic images, at a magnification of 10, of APP over neurons in the groups with LEFTY2 at different concentrations.

As shown in FIG. 5, compared with the group (group 1) without LEFTY2, the number of cells grown in the groups with LEFTY2 (group 2 to group 5) is significantly increased. Also, as shown in FIG. 6, compared with the group (group 1) without LEFTY2, the number and density of neuraxis in the groups with LEFTY2 (group 2 to group 5) are both significantly increased.

Figure 7:
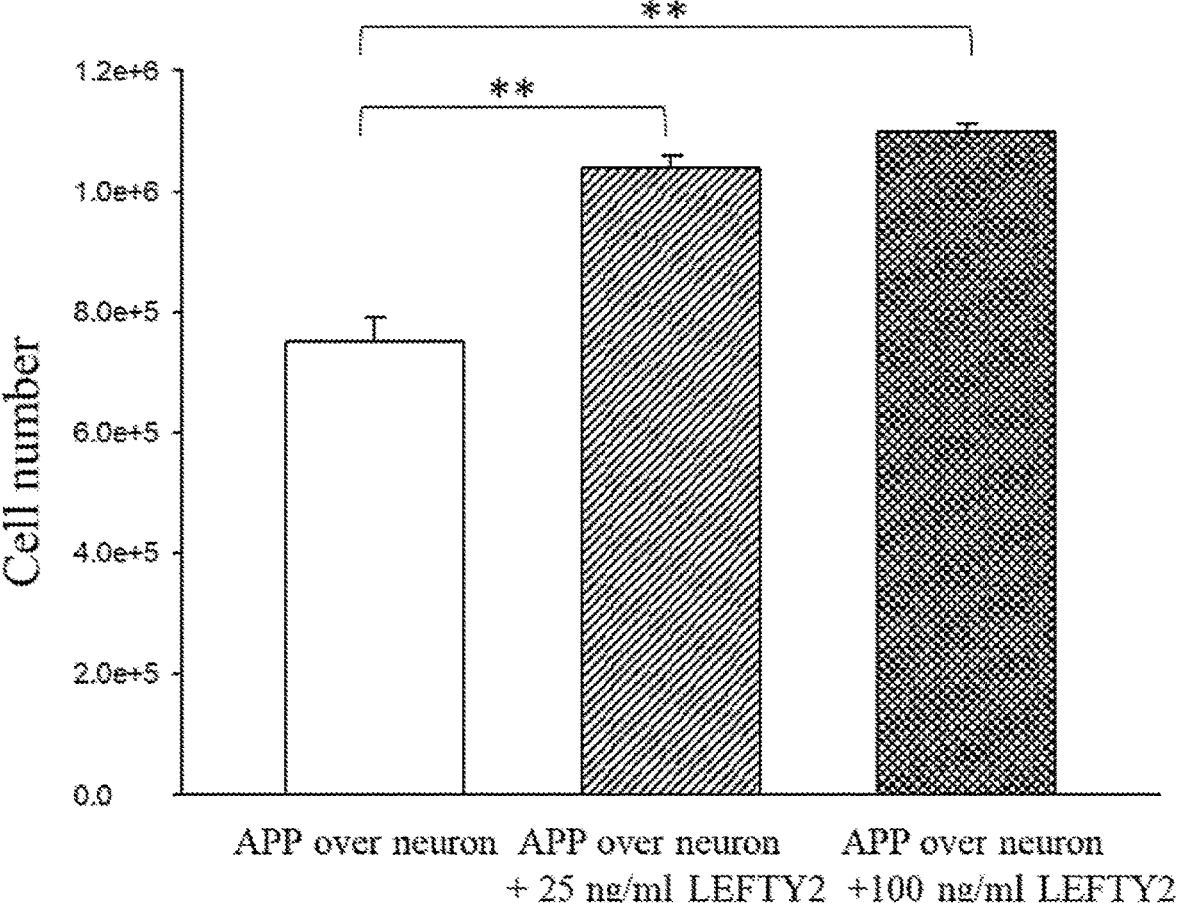
FIG. 7 illustrates the number of APP over neurons after treatment using 0 ng/ml, 25 ng/ml and 100 ng/ml LEFTY2 respectively.

Moreover, the number of APP over neurons in the group 1, group 2 and group 5 was respectively analyzed using a microscope. As shown in FIG. 7, the number of App over neurons in group 1 is $7.8 \times 10^5$, the number of App over neurons in group 2 is $1 \times 10^6$, the number of App over neurons in group 5 is $1.1 \times 10^6$, indicating that the groups with LEFTY2 at the lowest concentration of 25 ng/mL and the highest concentration of 100 ng/mL can both significantly increase the number of App over neurons.

Furthermore, from the time when a patient with Alzheimer's disease does not develop symptoms to the time when the patient is confirmed, Aβ1-42 and p-Tau181 of the patient's AP (Beta amyloid) will be gradually increased, and thus Aβ1-42 and p-Tau181 can be used as biomarkers for the disease progression or a therapeutic effect. It can be seen from the results shown in Table 4 and FIG. 8 that, compared with the group (group 1) without LEFTY2, Aβ1-42 in the groups with LEFTY2 (group 2 to group 5) is significantly reduced to less than 0.4 times; and it can be seen from the results shown in Table 3 and FIG. 9 that, compared with the group (group 1) without LEFTY2, p-Tau181 in the groups with LEFTY2 (group 2 to group 5) is significantly reduced to less than 0.5 times, and the concentration increase of LEFTY2 proteins shows a descending trend. Therefore, the LEFTY2 proteins can be deemed capable of effectively inhibiting Aβ1-42 and p-Tau181, which can slow down the disease progression of the patients with Alzheimer's disease.

Figure 10:
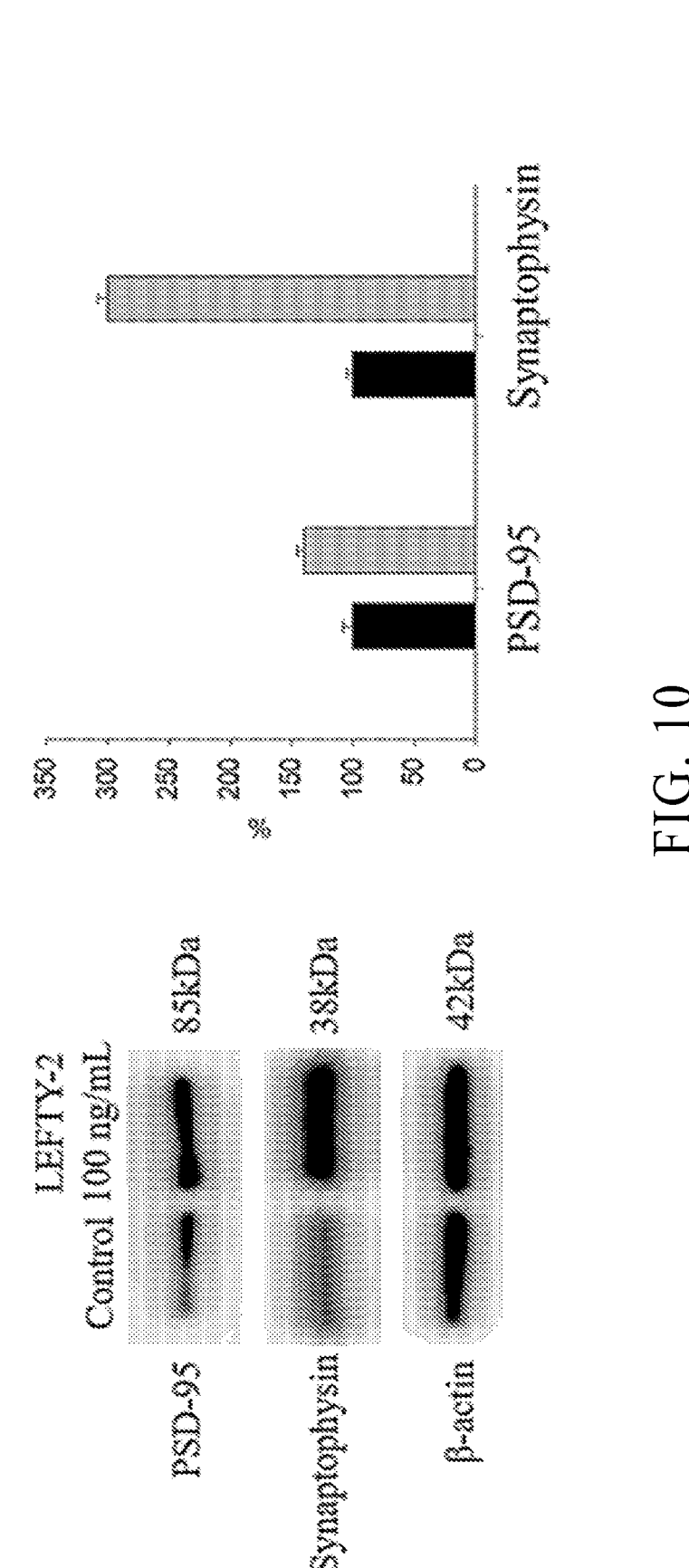
FIG. 10 is a comparison diagram illustrating the expression quantities of PSD-95 and synaptophysin in APP over neurons after treatment using 0 ng/ml and 100 ng/ml LEFTY2 respectively.

PSD-95 (Postsynaptic density protein 95) plays an important role in the synaptogenesis, synaptic maturation and stabilization of the synaptic zones in the neurons of the central nervous system of the brain. Synaptophysin plays an important role in the neurotransmission of hippocampal neurons. Therefore, PSD-95 and synaptophysin in the group without LEFTY2 (group 1) and the group with LEFTY2 (group 5) were analyzed using Western blot, with results shown in FIG. 10, confirming that the expression of both PSD-95 and synaptophysin in the neurons with LEFTY2 is significantly increased.

It can be seen from the above embodiments that, LEFTY2 can inhibit APP, and high-expression type ADSCs for highly expressing LEFTY2 can be produced by induction using nerve cells having mutations in the APP gene or by directly adding TSP-1.

In conclusion, the content of the present invention has been illustrated through the above-mentioned embodiments, but the present invention is not merely limited to these implementation modes. Those of common knowledge in the technical field of the present invention shall, without departing from the spirit and scope of the present invention, make various alterations and modifications. For example, new implementation modes obtained by combining or altering the technical contents illustrated in the above-mentioned embodiments, and these implementation modes shall certainly be deemed as one of the contents of the present invention. Therefore, the scope of protection claimed herein also includes the claims described later and the scope defined thereby.

What is claimed is:

1. A method for culturing high-expression type mesenchymal stem cells, by co-culturing initial mesenchymal stem cells with specific proteins in a second medium for 24 to 196 h, wherein the initial mesenchymal stem cells can be procured from different sources including adipose tissue, dental pulp, bone marrow tissue and umbilical cord tissue of mammals;

the second medium is a Neurobasal medium comprises 0.5-2 wt % of B-27 Supplement, 0.5-2 wt % of N-2 Supplement, 0.5-2 wt % of L-glutamine, 0.5-2 wt % of non-essential amino acids, 0.5-2 wt % of penicillin/streptomycin and 0.5-2 μg/mL of heparin;

the specific proteins are at least one of Thrombospondin-1, Galectin-7, Alpha-2-HS-glycoprotein, Sparc protein, Keratin type II cytoskeletal 74, Nucleophosmin and FSTL1 protein;

when the number of the initial mesenchymal stem cells is set as X1 and the concentration of the first specific protein in the medium is set as Y1 ng/ml, a ratio of X1 to Y1 is between $1 \times 10^6:100$ and $1 \times 10^6:1,000$; and the high-expression type mesenchymal stem cells can highly express LEFTY2 (Left-Right Determination Factor 2).

2. A High-expression type mesenchymal stem cell, which is prepared by the culturing method of claim 1 and capable of highly expressing LEFTY2.

* * * * *